United States Patent [19]
Kajander

[11] Patent Number: 5,135,851
[45] Date of Patent: Aug. 4, 1992

[54] CULTURE AND DETECTION METHOD FOR STERILE-FILTERABLE AUTONOMOUSLY REPLICATING BIOLOGICAL PARTICLES

[76] Inventor: E. Olavi Kajander, P.O. Box 6, SF-70211, Kuopio, Finland

[21] Appl. No.: 520,443

[22] Filed: May 8, 1990

[51] Int. Cl.$^5$ .......................... C12Q 1/04; C12Q 1/00; C12Q 1/68; G01N 33/53

[52] U.S. Cl. .................................... 435/34; 435/822; 435/7.32; 435/975; 435/6; 530/387.1; 530/391.3; 530/389.5; 436/518

[58] Field of Search .............. 364/513; 424/1.1, 85.91, 424/69.3–69.51; 514/237.8–616; 522/14–64; 523/115–118; 524/315–543; 530/316–423; 536/27–29; 544/162; 546/237–297; 548/215–234; 455/4, 7; 435/822.34, 7.32, 975.6; 436/518

[56] References Cited

PUBLICATIONS

Preston Activation Thermodynamics Enhancement of Adsorption to Filter's Masters Thesis, University of Florida 1985, pp. 69–72.
Jawetz et al. Review of Medical Microbiology, 17th Ed. Appleton & Lang, Los Altos Calif. 1987 pp. 306–309.
Roszak et al. Survival Strategies in the Natural Environment, Microbiol. Rev. 51:365–379 Sep. 1987.
Lee et al. A Rapid Multicolor Western Blot. J. Immuno. Chem. 106:27–30, 1988.
Kajander et al. Cell Wall Detective Bacteria Contaminate Cell Culture, Clin. Res. 37(2) 432A Apr. 28–May 1, 1989.

*Primary Examiner*—Christine Nucker
*Assistant Examiner*—David R. Preston
*Attorney, Agent, or Firm*—Burns, Doane, Swecker & Mathis

[57] ABSTRACT

Novel autonomously replicating biological particles resembling bacteria and having most surprising properties were discovered from cell culture sera and other biological samples alleged to be sterile according to the current testing methods. These slowly growing agents named Nanobacteria are smaller than any known cell-walled bacteria. They pass through sterile filters, even with pore sizes smaller than their diameter. They cannot be cultured on any standard microbiological media. With the isolation and detection methods provided here they are commonly detectable in animal or human serum. This patent holds for methods of their culture, detection, purification, and elimination and described the necessary reagents for that.

Autonomously replicating particles can be cultured in RPMI 1640, or in DMEM, or in other cell culture media. Optimal growth can be obtained by supplementing the culture medium with 10–20% sterile fetal bovine serum. Addition of small amounts of D,L or L selenomethionine together with nucleotide precursors may improve growth. Culture is started by addition of the test sample to the medium in a cell culture vial which is thereafter incubated under standard mammalian cell culture conditions for at least 15 days. Biological samples are preferably sterile-filtered before culture through 0.22 micron filters. The growth of Nanobacteria, if present, can be seen using microscopy at high magnification. The organisms can be made more visible by DNA staining and immunostaining done either separately or simultaneously to a fixed preparation. Nanobacteria can be cultured without mammalian cells, but co-culture together with an adherent cell line like 3T6 is useful because 3T6 cells can take Nanobacteria inside the cells. This aids the staining of the preparations. Intracellular agents are not lost during fixation and staining.

Nanobacterial antigens can be prepared by specific culture, harvest, purification and solubilization methods. Immunization of rabbits with the solubilized antigen (treatment with proteinase K and with 1 N HCl) produces highly specific antibodies to Nanobacteria. Gamma-irradiation of culture serum at 2.5–4.0 megarads, preferably in addition with treatment using solid-phase bound antibodies enables preparation of Nanobacteria-free serum. Use of this serum creates sterile culture medium for the culture and detection of Nanobacteria. Double staining combining Hoechst No. 33258 stain and immunofluorescence specifically distinguishes Nanobacteria from other cell culture contaminants.

24 Claims, 7 Drawing Sheets

CULTURE AND DETECTION METHOD FOR STERILE-FILTERABLE AUTONOMOUSLY REPLICATING BIOLOGICAL PARTICLES

BACKGROUND OF THE INVENTION

1. Description of the Invention

The present invention is concerned with the identification, detection and isolation of a novel autonomously replicating biological particle. The biological particle is a bacteria-like organism that readily passes through sterile filters of pore size of 0.3 μm. It is a member of a novel genus hereby referred to as Nanobacterium and has been accorded a special name.

2. Description of the Prior Art

It is generally believed that animal blood and tissues, except those facing external surfaces, such as the skin and mucosa, are sterile. This idea is primarily based on microbiological culture experiments utilizing culture media optimized for the culture of pathogenic bacteria generally associated with humans and animals. By utilizing special culture media, however, cell-wall defective bacterial variants (oftentimes referred to as bacterial L-forms) have been identified from a variety of living material. Bacterial L-forms have been detected using special culture media in approximately fifty percent of both healthy and sick humans. Conventional culture methods do not support the growth of those microbes and the possible biological significance of their presence in blood and tissues is not known at this time.

The special bacterial L-form culture medium is typically a hyperosmolar medium containing a sugar such as sucrose, sodium chloride or polyvinylpyrrolidone (PVP) as a stabilizer; brain heart infusion broth or other bacteriological nutrient source; agar; protein such as horse serum; and an antibiotic such as penicillin. Penicillin and other antibiotics prevent peptidoglycan synthesis which both convert normal bacteria to L-forms and prevent the reversion of L-forms back to cell wall containing bacteria.

Animal or human serum is widely utilized in cell culture as a growth supporter. Serum for cell culture is collected from animals at slaughterhouses. Animal serum has been recognized as a major source of contamination in cell culture. For instance, mycoplasma contamination was very common before commercial cell culture serum was screened for the presence of mycoplasma.

Animal or human serum is sterilized using a step-wise sterile filtration procedure at high porosity. The final and smallest filter size is generally in the range of about 0.22 μm to 0.1 μm. Common bacteria are retained by 0.45 μm filters. The sterility of the final product is typically detected by taking samples from the serum lot and incubating them at 25° C. and 37° C. for one or two days and then performing standard microbiological culture assays on agar media or filters. The cultures are then examined at intervals up to two weeks. The conventional culture method will detect bacteria growing under culture conditions but will not show fastidious or noncolony forming bacteria.

Bacterial L-forms or cell wall defective bacteria have been recognized for some time. Such bacteria have been found in many types of organisms including humans. Bacterial L-forms readily pass through sterile filtration. Thus, since bacterial L-forms may be present in animal sera and animal sera are often used in cell cultures and blood products, the bacterial L-forms remain in those compositions since they are usually sterilized by filtration.

The presence of bacterial L-forms in cell cultures and inside cultured cells, and cell morphology during such an infection have been studied by several authors. These studies were carried out by inoculating cultured cells with artificially produced bacterial L-forms. Only one published report describes a cell culture being contaminated by something resembling a bacterial L-form originating from nature, that is, outside the laboratory. That report by I. Willers, S. Singh, K. R. Held, and H. W. Goedde, "High HPRT Activity in Fibroblasts from Patients with Lesch-Nyhan Syndrome due to Bacterial 'L-form' Contamination", Adv. Exp. Med. Biol., Vol. 122, pp. 327-331, 1980) discloses that fibroblasts from a Less-Nyhan patient were positive for HPRT enzyme activity. This enzyme activity is totally absent from Less-Nyhan fibroblasts, and thus the contaminants caused an erroneous result in testing of this biochemical marker of importance for genetic counseling. This report is also the only publication indicating that cell culture serum is a source for L-form infection. However, the organisms were neither identified nor was their nature provided in any detail.

Bacteriological sterility of cell cultures is an absolute requirement for metabolic as well as other types of experiments in order to obtain valid results. Bacteria smaller than the porosity of filters used for sterilization or bacteria having elastic cell walls (L-forms) can readily pass through the filter and thus prevent adequate sterilization. If the contaminating organisms are not detected by the methods used for confirming bacteriological sterility, the product, e.g., the sera, is likely to form a very potent hazard for cell culture experiments. The available bacteriological methods are insufficient for the detection of such contamination.

The present inventor has successfully isolated and cultivated a new bacterial contaminant in substantially pure form by developing new methods for cultivating and detecting such filterable bacteria discovered from commercial cell culture sera.

SUMMARY OF THE INVENTION

Applicant has surprisingly isolated in biologically pure form a novel bacteria now designated by the genus Nanobacterium. The microorganism has been isolated by the inventor and three samples, Nanobacterium sanquineum were deposited at the DSM under the Budapest Treaty on the International Recognition of the Deposit of Microorganisms for the Purposes of Patent (Budapest Treaty) as Numbers 5819, 5820 and 5821 on Mar. 2, 1990. It is possible that there are a number of different species of bacteria which have the characteristics of the genus Nanobacterium.

The present invention is related to a novel method for identifying or detecting bacteria of the genus Nanobacterium in a biological or commercial sample. Samples may include blood, serum, tissue fluids, tissues, cells or the like.

The subject invention is also related to a process for the cultivation of bacteria of the genus Nanobacterium.

The present invention is intended to provide a test kit for identifying the presence of bacteria of the genus Nanobacterium in biological samples such as cell culture sera, cell culture media and the like.

Further, the present invention is directed to a method for preparing and purifying Nanobacteria. e.g., for testing purposes.

In addition, the subject invention is concerned with the diminution and elimination of Nanobacteria in serum.

The present invention also includes the use of highly specific antibodies obtained using specifically purified Nanobacteria. The method combines simultaneous staining with labelled antibody and with a DNA stain using, e.g., 3T6 cells as an indicator cell culture for test purposes.

DESCRIPTION OF THE PREFERRED EMBODIMENTS

Figure 1:
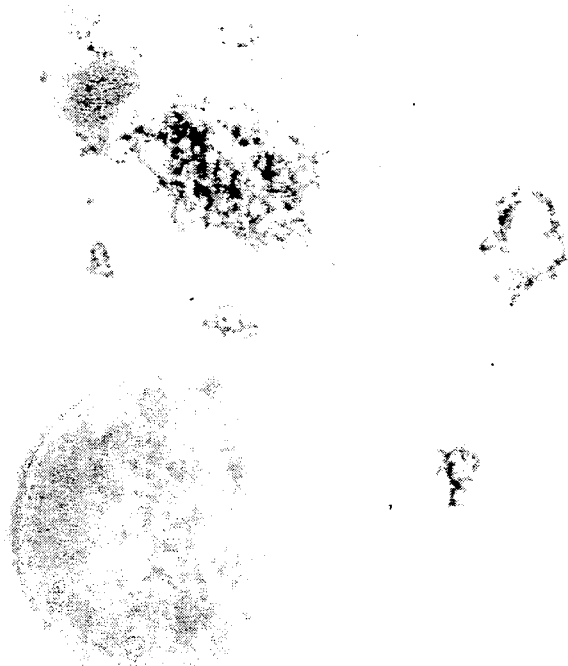
FIG. 1 is a transmission electron micrograph of the coccoid form of a bacteria of the genus Nanobacterium where the cell membrane and cell wall are observed (bar 100 nm).
Figure 1:

The applicant has succeeded in isolating unidentified bacteria-like particles present in biological samples such as commercial cell culture sera. Those cell culture sera are alleged to be sterile by the manufacturer. The unidentified bacteria, now referred to as the genus Nanobacterium have the following characteristics:

Shape: coccoid (most common) or bacillar.

Degree of Aggregation: appears to depend on the culture medium and culture time; may be present alone (single), in pairs, in tetrads or in clusters.

Size: a) inner (intermembrane) diameter: approximately 0.1 to 0.25 $\mu$m for the coccoid form; similar diameter for the smaller dimension of the bacillar forms with the large dimension being about twice the size of the smaller diameter.

b) outer diameter: approximately 0.1 to 0.5 $\mu$m for the coccoid form including the cell wall (but not the slime); occasionally a loose capsule is observed after a long culture time; the bacillar form can be larger and longer.

Cell Wall: The typical cell envelope structure contains a cytoplasmic membrane and a cell wall. The membrane resembles the usual unit membrane under electron microscopy. The thickness of the cell wall varies greatly but is typically about 50 to 100 nm in bacteria cultured for several weeks. A loose outer capsule may be present. Slime may also be present. Using electron microscopy, the cell wall structure appears to resemble a gram-positive envelope.

Presence in Nature: typically present in animal and human blood, serum, tissue and tissue fluids.

Culture Properties: do not appear to grow on any standard or commonly used bacteriological media.

Staining Properties: very difficult to stain due to exceptional surface properties causing problems in sample fixation and staining. For example, it cannot be stained using gram stain or giamsa stain.

Biochemical Characteristics: contain protein, lipid, carbohydrate, DNA, RNA, ATP and amino acids.

Growth Rate: Growth is slow and typical doubling time is about one to five days.

Resistance to antibiotics: under described culture conditions very resistant to antibiotics commonly used in cell culture, such antibiotics typically include penicillin, streptomycin, gentamicin, kanamycin and the like.

Physical and chemical resistance: The structure of these organisms tolerates harsh conditions without disruption, e.g. prolonged treatment with ultrasound; freezing and thawing cycles; solutions of low osmolarity; high temperatures (even heating in the presence of sodium dodecyl sulphate); extraction with organic solvents such as chloroform, acetone, phenol and the like; and proteolytic enzymes such as proteinase K and lysozyme, once again, even in the presence of sodium dodecyl sulphate.

These organisms differ from "normal" known bacterial species in several ways. Their size is smaller than that of known bacteria having a cell wall. They pass through sterile filters intended to retain bacteria. Although their cell wall resembles when observed via electron microscopy the cell wall ram-positive bacteria, these bacteria will not stain gram-positively as do most other bacteria with this cell wall structure. A known notable exception is bacteria of the genus Mycobacterium. This staining property of the unidentified contaminants and the Mycobacteria can possibly be attributed to an impermeable cell wall. Both Nanobacteria and Mycobacteria are Ziel-Nielsen positive.

The cell wall of Nanobacteria is resistant to proteolytic enzymes that digest the cell wall of micrococci or other gram-positive bacteria, e.g., lysozyme. The unidentified organisms do not grow detectably on any commonly used bacteriological culture media. In cell culture, the unidentified organisms do not turn the medium opaque nor do they change the color of the medium as do common bacteria.

Likewise, Nanobacteria differ from bacterial L-forms, in that they have a cell wall, although the thickness of the cell wall varies greatly. Nanobacteria do not require a hyperosmolar stabilized medium as do bacterial L-forms. However, osmotically stable L-form variants of common bacterial contaminants have been produced experimentally. Nanobacteria do not revert to normal bacteria. Bacterial L-forms usually revert back to a cell-walled (original) form. At the same time, bacterial L-forms also acquire their original growth properties and possibly their original pathogenicity.

Nanobacteria never gain the ability to grow on common bacteriological media, and do not form colonies resembling any known bacterial species as do bacterial L-forms.

Applicant has developed a culture and detection method that allows the propagation, microscopic detection and immunological verification of previously unidentified bacterial agents, i.e., bacteria of the genus Nanobacterium. which contaminates serum and serum products as well as other biological material. In addition, the described culture method supports the growth of common bacteria and osmotically stable bacterial variants, i.e., bacterial L-forms as well are enabling their simultaneous detection. Thus, all bacterial forms excluding strictly intracellular parasites that may contaminate the sample, are detected. With the double staining method (DNA stain plus immunostaining), Nanobacteria can be specifically detected in spite of other bacteria being present in a sample. Alternatively, Nanobacteria alone may be selectively cultured and detected after filtration of the sample through 0.22 μm sterile filter available from commercial sources, e.g., Millipore.

Nanobacteria cannot be grown on standard media for bacteria, and thus they escape detection when using standard culture methods. The detection of the extremely small unidentified bacteria is hampered by their size, which, e.g., in commercial cell culture isolates, is smaller than 0.5 μm. Thus, their detection via light microscopy is possible only with the best microscopes having maximum resolution. Tissue culture laboratories are seldom equipped with such microscopes. Further, these bacteria are difficult to collect since centrifugation is difficult. They are also readily lost since they do not adhere to glass, and they cannot be stained with common bacteriological stains. The growth requirements of species of bacteria of the genus Nanobacterium are quite similar. The growth requirements can be met using standard tissue culture media. This is likely because these bacteria are adapted for living inside the mammalian body.

The culture and detection method cf the present invention rests on the principle of culturing the bacteria under conditions similar to tissue culture. Any standard tissue culture media is useful in the practice of the present invention. Cell or tissue culture media are generally used to culture mammalian cells. During culture, Nanobacteria become visible under light microscopy due to their multiplication, aggregation, secretion of slime and/or the thickening of their cell envelope. Their detection is aided by providing killed bacteria of the genus Nanobacterium for comparison as a control.

Furthermore, a modification of the Hoechst DNA staining method has been developed to verify that the particles contain DNA. This method involves using Hoechst No. 33258 stain. Nanobacteria are pelleted by centrifuging the well-mixed culture medium at at least 14,000 g for at least 20 minutes. The pellet is then suspended in a drop of phosphate buffered saline or saline, and spread on a cover glass (or on an objective glass). An equal volume of commercial 25% glutaraldehyde solution (range 1-25% in phosphate buffered saline) is layered on the sample area. Glutaraldehyde functions as a fixative that aids in attaching the Nanobacteria on the glass. After 30 minutes the glass is immersed into Carnoy's fixative (1:3 acetic acid:methanol) for another 30 minutes. After drying at room temperature, the glass is immersed into Hoechst stain solution (0.5 mg/l is the preferred concentration in phosphate buffered saline). After 30 minutes, the glass is washed by immersing twice in water, 1 minute for each wash. Thereafter, the glass is mounted with a suitable mounting medium such as 50% glycerol in phosphate buffered saline. (Sample side facing the mounting medium). The preparation can then be viewed by standard fluorescence microscopy using the commonly available filter sets intended for use with Hoechst 33258 stain as described by T. R. Chen, "In situ Detection of Mycoplasma Contamination in Cell Cultures by Fluorescent Hoechst 33258 Stain", *Exp. Cell Res.*, Vol 104, pp. 255-262, (1977).

Suitable culture media include those identified below:
DMEM/Ham's F-12 (1:1)
Basal Media Eagle
CMRL 1066 Media
Dulbecco's Modified Eagle Media
Fischer's Media
Glasgow Minimum Essential Media (BHK-21)
Hybridoma Media (Serum Free)
Iscove's Modified Dulbecco's Media
Leibovitz's L-15 Media
McCoy's Media
Media 199
Minimum Essential Media (MEM)
NCTC Media
Medium NCTC-135
F-10 Nutrient Mixture
F-12 Nutrient Mixture
Opti-MEM I Reduced Serum Medium
RPMI Medium 1630
RPMI Medium 1640
Waymouth's Media
William's Media E
BGJb Media
DMEM and its modifications where glucose levels vary between 1 to 4.5 g/liter All of the foregoing cell culture media are distributed by Gibco Co. and relate to the culture of mammalian cells. The media are marketed with modifications in buffering systems and contain Earle's or Hanks' salts with or without HEPES.

A preferred embodiment of the present invention involves a synthetic medium suitable for the growth of Nanobacterium by fulfilling their growth requirements. The liquid medium comprises a standard tissue culture medium known as RPMI 1640. This medium is a standardized composition of amino acids, salts, etc. which can be obtained from Gibco (Uxbridge, Middlesex, U.K.).

The components of the culture medium should be dissolved in essentially sterile water. The quality of water used is extremely important, since water can contain cytotoxic impurities for the unidentified agents. Care must be taken to avoid water as a source of contamination. Tap water, deionized water or sterile water for injection, for instance, may all be adequate if their sterility is checked in advance.

The culture media can also be solidified using agar or agarose. However, once again, agar or agarose may contain cytotoxic impurities. The presence of Nanobacteria is difficult to detect via microscopy when using agar or agarose since solid media have inferior microscopic properties. Thus, solid media are generally inferior to liquid media in the detection of the presence of Nanobacteria.

Growth is also optionally stimulated by the addition of nucleotide precursors and to the supplements such as L or D,L-selenomethionine. Thus, the medium is preferably supplemented with a mixture (50-100x concentrate) prepared separately from D,L-selenomethionine, adenosine, thymidine, uracil, guanine and cytosine all of which can be obtained from Sigma Chemical Co., St. Louis, Mo. For example, the 100x-concentrate contains 10 mM DL-selenomethionine and 1 mM by each of the following compounds: adenosine, thymidine, uracil, guanine and cytosine, dissolved in a solvent. The final medium is prepared by adding 1 ml of the dissolved 100 x concentrate to 99 ml of the basal medium. In the preparation of the basal medium and of the supplement, a deionized distilled water is utilized. Standard procedures in utilizing pharmaceutical grade components and biologically sterilized equipment are followed.

Growth under tissue culture conditions occurs more rapidly in the presence of 10 to 30% animal serum, but this is not an absolute requirement. Serum addition also shortens the adaptation period usually found in the beginning of the culture. Nanobacteria generally have a lag time for growth. This lag time typically varies anywhere from one day to one week. Gamma-irradiated sterile fetal bovine serum may preferably be added to a final concentration of 20%. Fetal bovine serum intended for use in sterility testing or culture of a certain species of the Nanobacteria bacteria is gamma-irradiated with a dose and for a time sufficient to kill Nanobacteria. The gamma-radiation is generally in the range of about 2.5 to 4.0 regarads, preferably 3 megarads. During gamma-irradiation, the serum may be in a frozen or melted state. The fetal bovine serum used for this purpose must not contain the Nanobacteria contaminants in detectable amounts, because the contaminant particles remain in the serum after irradiation. Although irradiation prevents their multiplication, killed contaminants may interfere with detection of the possible presence of Nanobacteria in the examined samples. The killed bacteria retain their shape and can be used as an aid in interpreting the microscopy during Nanobacteria testing (killed standard).

Typical culture conditions may involve incubation at 37° C. in an atmosphere of 5–10% $CO_2$ and 95–93% air (moisture about 90%). The conditions are generally standard cell culture conditions. It may be advantageous to incuoate the vial with the flat side facing down.

Nanobacteria can be removed from serum by use of adsorption with specific antibodies recognizing Nanobacterial antigens. The antibodies are immobilized on a suitable surface, e.g., on a vinyl immunosorbent material or on Sepharose gel beads, preferably using well-documented covalent immobilization methods like coupling with either glutaraldehyde or with cyanogen bromide. Serum is then brought into a close contact with the immobilized antibody. The antibody coated material should preferably be packed in a compact form like a column or a pack of filters. The antibodies will then bind Nanobacteria which will then become immobilized. This takes place within minutes or a few hours. The procedure can be carried out at the temperature of 0 to 60 degrees centigrade. Nanobacteria-free serum can be recovered simply by eluting or collecting the serum. Removal of Nanobacteria with the adsorption method is preferably done before gamma-irradiation.

Antibodies to Nanobacteria are preferably made by immunizing animals like rabbits with specifically purified Nanobacteria or with an extract obtained from purified Nanobacteria. The special purification of the Nanobacteria antigen is important because Nanobacterial preparations may contain adsorbed or precipitated impurities from their culture medium that typically contain highly immunogenic serum. Purification can utilize exceptional properties of Nanobacteria. They are highly resistant to the actions of practically all proteinases, like proteinase K, trypsin, papain, and the like. They can also be washed with organic solvents like chloroform, ether and alcohols. Furthermore, their structure endures extreme pH values like pH 1 to 14. Thus, washing with strong alkaline solutions may result in removal of impurities. A solubilized antigen offers many advantages for immunization and especially for detection of antibodies. Such a preparation can be achieved by incubating Nanobacteria with a strong acid. Typically, this can be done with 1 N hydrochloric acid (range 0.1 to 2.0 N HCl).

Highly Nanobacteria specific antiserum can be prepared in animals, e.g., in rabbits, as follows: Nanobacteria are cultured and thereafter harvested by centrifugation at least at 14,000 g for at least 20 minutes according to the conditions referred to in this application. The pellet is incubated with proteinase K added at 0.5 mg/ml (range 0.01 to 100 mg/ml) in a small volume of buffer like phosphate buffered saline. Typically, incubation is carried out at 37 degrees centigrate, but a broad range of temperatures are suitable as well, for 1 hour (range 0.1 to 48 hours). The temperature need only be sufficient to allow incubation. The incubation results in minimal loss of Nanobacteria. It is highly effective in degrading serum proteins. Degradation products and the proteinase can be easily removed with a buffer like phosphate buffered saline and pure Nanobacteria are collected by centrifugation. Thereafter, Nanobacteria may be used as an antigen or Nanobacteria are solubilized by incubation with 1 N HCl for 1 minute (range 0.1 to 10 minutes) in a suitable small volume at room temperature, but other temperatures can be used as well if incubation time is modified. Incubation is stopped by neutralizing the mixture with an alkaline solution or with buffer. Typically, 1 N NaOH or 1 N KOH is used in equal volume to the amount of HCl volume used. This treatment has now resulted in a solubilized antigenic preparation which is viscous like a gel. The present inventor has found that this kind of extract was highly immunogenic. Given preferably several times at about one week intervals intravenously, intraperitoneally or subcutaneously into a rabbit, it resulted in the formation of high titers of highly specific antibody binding specifically to Nanobacteria as detected by immunofluorescence microscopy.

Nanobacteria could also be purified from serum and from Nanobacteria cultures by use of filters of small pore size. Typically, a sample of Nanobacteria culture was filtered with a commercial filter available from Millipore having a pore size of about 0.1 or preferably 0.05 microns. In a small scale, filter tests were performed using Swinnex Disc Filter Holder loaded with a Fluoropore, MF-Millipore or Durapore filter with appropriate pore size (all materials available from Millipore). If performed under relatively low pressure, most of the Nanobacteria present were retained in the filter. They can be washed and purified by incubating with a proteinase, e.g., with proteinase K under conditions described above for Nanobacteria purification but performed inside the filter holder. After washing degradation products away, Nanobacteria can be collected by changing the flow direction of the system to the opposite direction (backwards elution).

Specific methods for purification of the Nanobacteria and preparation of their solubilized antigens result in material that can be used as an antigen in immunization of animals or humans, and in construction of immunoassays for detection of Nanobacteria, or for detection of antibodies against Nanobacteria. Also, antibodies against Nanobacteria can be bound and purified with them. Both Nanobacteria and the solubilized extract can be bound covalently to vinyl ELISA immunosorbent plates using well-known glutaraldehyde coupling to vinyl. Such plates performed excellently in Elisa detection of antibodies against Nanobacteria.

Specific antibodies recognizing Nanobacteria can bind Nanobacteria. They can be utilized to immobilize Nanobacteria or to remove Nanobacteria from a biological sample in the purposes of elimination, assay and purification of Nanobacteria. Antibodies can be used in many ways to construct an immunoassay for Nanobacteria. Also, the antibodies may find use in elimination of Nanobacteria from cell cultures or from animals or from humans. Further, the antibodies may be applicable for purification of products derived from cell cultures, animals or humans. These may include blood, serum and their products, or cells and organs, or in vitro cultured products including cells.

An important application of antibodies recognizing Nanobacteria is their use in immunofluorescence assays and stainings to detect specifically Nanobacteria. For that purpose the antibodies may be coupled with any fluorescent label suitable for microscopy. Alternatively, the antibody bound to Nanobacteria antigen may be visualized with another antibody or protein A or protein G carrying a label. Immunofluorescent detection can be used in immunofluorescence microscopy in fluorescence activated cell sorting and in fluorescence based immunosorbent types of assays.

As a further improvement of the detection of Nanobacteria, a method was developed combining staining with a fluorescent DNA stain and immunofluorescence with antibodies to Nanobacteria labelled with a fluorescent label, or visualized with another antibody, or protein A, or protein G labelled with a fluorescent label. Both stainings are preferably done simultaneously or one after the other to the same preparation. Staining with a DNA stain will reveal practically all microorganisms. Staining with specific antibodies will reveal only Nanobacteria. Both images or signals can be seen or analyzed simply by changing appropriate filter sets applicable for the used DNA stain and for the used fluorescent label of the antibody detection system. Such a double staining method is described in detail in Example II.

The double staining method developed here was optimized for use with samples from 3T6 cell culture. 3T6 cells are exceptionally suitable for detection of Nanobacteria because they internalize Nanobacteria effectively allowing for the use of a mild fixation protocol described in Example II. Internalized Nanobacteria are not washed away from the sample in the necessary washing steps involved in an immunostaining. 3T6 cells also show minimal autofluorescence under the described conditions. However, other cell lines like 3T3, BHK, CHO and other adherent cell cultures may be used.

In the described test, 3T6 serves as an indicator cell culture into which a test sample is inoculated. 3T6 cells together with the sample are then cultured under cell culture conditions for a certain time, typically 3 days (range 1 hour to 10 days). During this time, microbes like mycoplasmas, common bacteria and Nanobacteria multiply in the culture. For optimizing multiplication, antibiotics are not included. Thereafter, the possible presence of microbes is detected by staining with a suitable DNA stain like Hoechst No. 33258 in combination with an immunofluorescent staining with an antibody detection system visualizing Nanobacteria. Initially, 3T6 cells are washed with a suitable buffer like phosphate buffered saline. Then they are fixed with formaldehyde typically in phosphate buffered saline at the concentration of about 3% (range 0.1–30%). Fixation time is typically minutes or hours and can be carried out at a temperature of about 0° to 40° C., preferably at room temperature. Glutaraldehyde solutions may also be used, but regretably they may cause strong autofluorescence in mammalian cells. Thereafter, the preparation is washed and then subjected to a brief permeabilization treatment, e.g., with Triton X-100 (0.5% for 1–20 minutes) in phosphate buffered saline. Then the preparation is stained with Hoechst 33258 at about 0.5 mg/l and with a suitable fluorescent antibody preparation, again in phosphate buffered saline. After sufficient labelling or staining, typically after 30 minutes (range 1 minute to 1000 minutes), excess label or stain is washed away and the preparation is analyzed by microscopy or by other suitable methods to visualize the fluorescence of both labels.

The 3T6 indicator culture method together with the described double staining method serves as a test system to screen cell culture samples, sera, media or other biological samples to detect microorganisms, especially Nanobacteria. The staining method distinguishes Nanobacteria from other possible microbes. Practically all possible microbes are detected.

The described double staining method can be used also to detect the presence of microbes on membrane filters, especially the presence of Nanobacteria. This application can be used to construct concentration-detection methods utilizing membrane filters with small pore sizes to collect Nanobacteria (see the purification method for Nanobacteria). Nanobacteria are thereafter specifically detected by staining or by culture. After culture, the staining can be used to verify the result. Furthermore, the double staining may be used with fluorescent cell sorting systems to detect and even to isolate Nanobacteria.

Culture of bacteria of the genus Nanobacterium is carried out by adding a biological or commercial sample to the culture medium typically contained in a vial using standard sterile technique. The cultures are then incubated in a standard tissue culture incubator at a suitable temperature, generally about 20° to 50° C., preferably about 37° C.

The cultures can be made in any sterile tissue culture dish or flask or bacteriological dish. Preferably tissue culture flasks should be used, e.g., from Nunc in Roskilde, Denmark. A 25 ml flask is suitable for the culture of the samples. Generally, within about five minutes or less, a suitable amount, preferably approximately eight ml of a tissue culture media such as an RPMI 1640 medium preferably containing a D,L-selenomethionine nucleotide precursor supplement at about 0.001 x to 10 x, preferably 1 x is added to the flask. Then approximately 2 ml of the tested serum sample is added. These steps are carried out using sterile technique.

Then the flask is transferred to the incubator and cultured. Either the top of the flask is loosened or closed after flushing with approximately 5 to 10% $CO_2$ typically in air. If dishes are used, the incubation should preferably be carried out in a humid incubator in an atmosphere of approximately 90 to 95% air and approximately 10 to 5% $CO_2$. A range of about 80 to 99% air and 20 to 1% $CO_2$ is suitable.

Incubation for at least 15 days in a liquid media is needed for the microscopic detection of the Nanobacteria contaminants. The dishes or flasks should be viewed at an interval of every 2 or 3 days for the appearance of visible tiny bacteria. If present, the Nanobacteria can be seen typically after about 5 to 10 days culture. For reliable interpretation, a magnification of at least 400-fold should preferably be used. Phase or differential interference contrast microscopy will show the Nanobacteria more easily. The reference bacteria (gamma-irradiated) should be viewed microscopically at the same time in order to make it clear that the tiny organisms can indeed be observed with a microscope. They also provide a reference or control for the visual characteristics of Nanobacteria.

The culture of the unidentified bacteria can be done from serum, body fluid or tissue, preferably after homogenization, even from samples containing common bacteria. Common bacteria are optionally eliminated by filtration through 0.22 μm filters. Thereafter, a culture is started from the filtered sample.

The presence of bacteria of the genus Nanobacterium in cell cultures can be detected after centrifuging the cells at low g values (approximately 1 to 1000 g) and by using the supernatant as a sample. Alternatively, the cell pellet can be disrupted and the solution may be used as a sample (preferably filtered through 0.22 μm filter). This latter technique will generally bring intracellular forms to the sample.

Figure 2:
FIG. 2 is a transmission electron micrograph of a bacteria of the genus Nanobacterium, and slime can be observed in the bottom of the micrograph.
Figure 3:
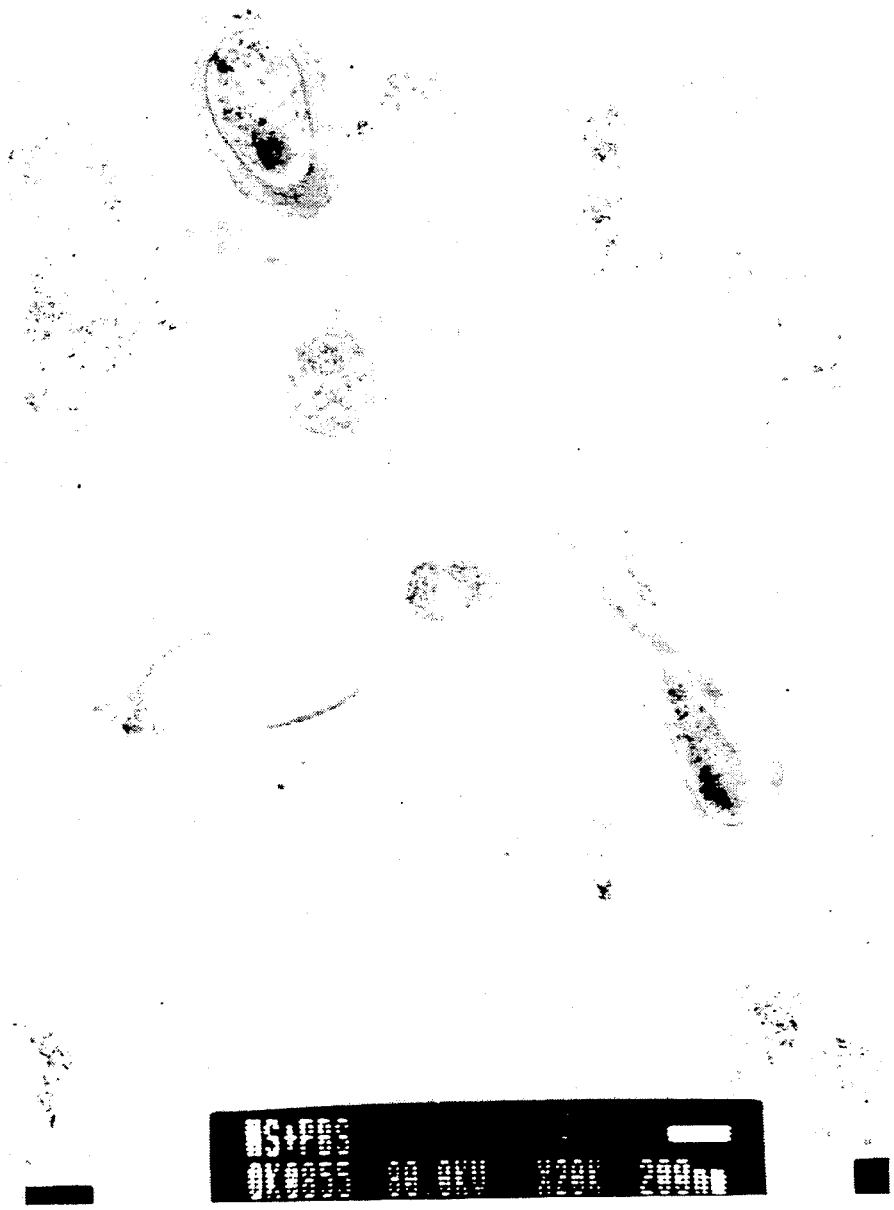
FIG. 3 is a transmission electron micrograph of the bacillar form of a bacteria of the genus Nanobacterium.
Figure 4:
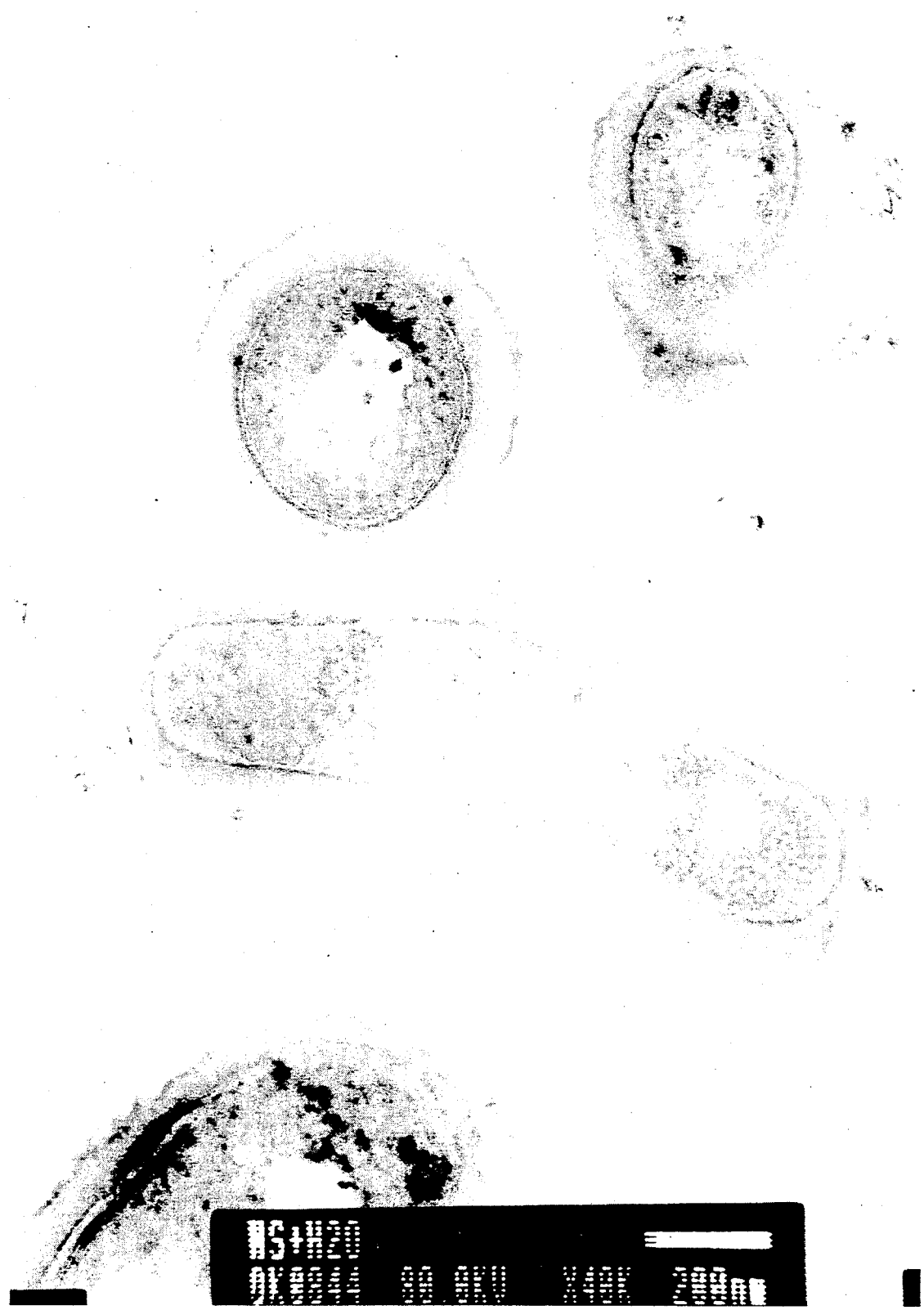
FIG. 4 is a transmission electron micrograph of the coccoid form and the bacillar form of bacteria of the genus Nanobacterium.
Figure 5:
FIG. 5 is a transmission electron micrograph using negative staining of a bacteria of the genus Nanobacterium.
Figure 6:
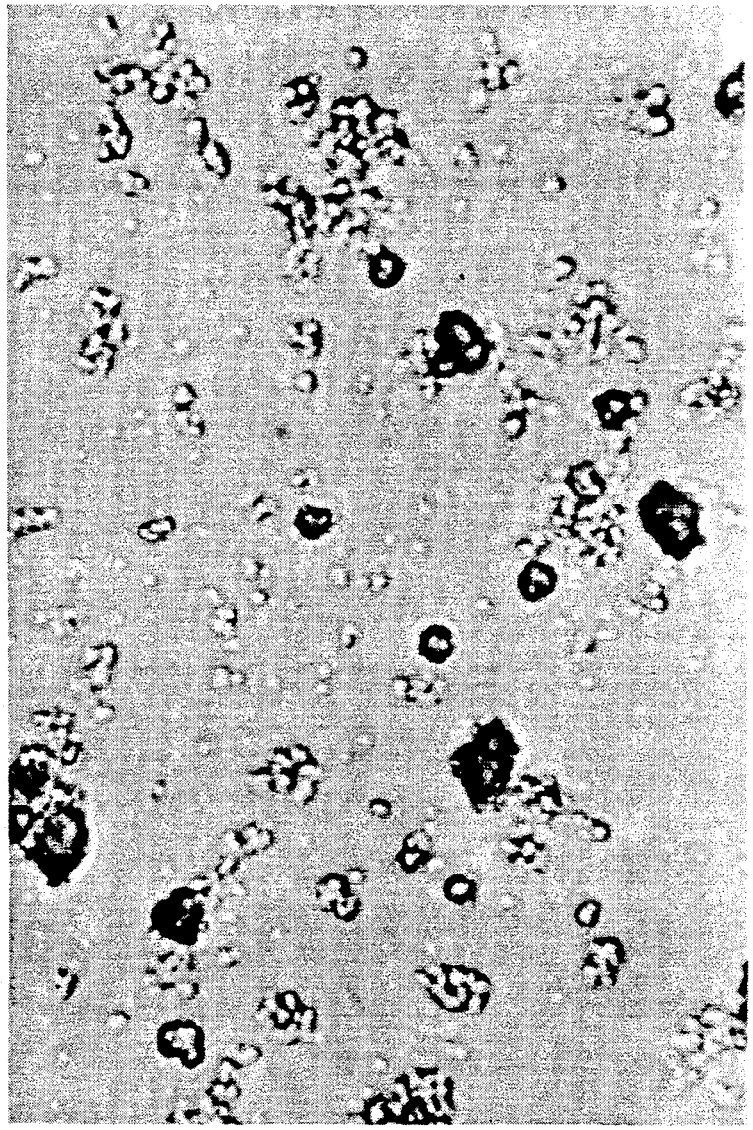
FIG. 6 is a phase-contrast view magnification 1600X) of bacteria of the genus Nanobacterium depicting the aggregation pattern seen using older cultures.
Figure 7:
FIG. 7 is a micrograph of MG-63 cells (osteosarcoma) cultured on glass with a culture medium contaminated with Nanobacteria using Jones' silver staining where the black-stained Nanobacteria are located both extra cellularly and around the nuclear area.

The criteria for a positive culture is detectable growth of organisms having the criteria of appearance, shape, size, filterability and lack of growth on common bacterial media like chocolate agar or blood agar as noted above. Further, verification can be done by immunofluorescence. Common bacteria will multiply very rapidly in the medium and they can be visually observed after culturing for one or two days. FIGS. 1 through 7 depict bacteria of the genus Nanobacterium.

A variety of DNA stains are useful in the practice of the present invention. Such stains include Hoechst stain No. 33258. Hoechst stain No. 33342, Hoechst stain No. 2495, Dapi, Acridine Orange, and the like. Hoechst stain 33258 is preferred.

As a control, medium samples should be taken, handled, and incubated in the same way as the tested samples. No growth should take place in control cultures. If growth occurs in control cultures, the test is not valid, since this is an indication of outside contamination.

A test kit is also provided which comprises tissue culture medium sufficient for allowing the culture of bacteria of the genus Nanobacterium, gamma-irradiated bacteria of the genus Nanobacterium as a control and a nucleic acid stain suitable for staining bacteria of the genus Nanobacterium. In addition, specific antibodies recognizing Nanobacterial antigens are optionally provided. For culturing purposes, Nanobacteria-free serum may also be provided. Also, an uncontaminated culture of 3T6 cells may be provided.

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claims.

EXAMPLE I

A medium was prepared by mixing 5 ml of 100 x D,L-selenomethionine supplement to 495 ml of RPMI 1640 as identified in Table I for a total volume of 500 ml. A description of media, RPMI 1640 appears in Moore et al, "Culture of Normal Human Leucocytes", J.A.M.A., 199, 519–524 (1962). Next, approximately 8 ml portions were then pipetted to 25 ml culture flasks and samples of 2 ml of the tested commercial cell culture sera were added. In the control experiments only medium was added. The flasks were incubated at 37° C. in a humidified incubator containing 95% air and 5% $CO_2$ for 15 days. The cultures were inspected daily using an Olympus CK2 inverted microscope (Olympus, Japan) at a magnification of 400 x utilizing phase-contrast microscopy. Contaminants appeared barely visible under the microscope at various times. The sample was scored +++, if the criteria characteristic of Nanobacteria were observed within approximately 24 hours of the start of the culture. Those cultures scored ++, in which contaminants could be detected only after approximately 5 to 10 days culture, + was given to those cultures which showed visible contaminants approximately 10 to 15 days after the start of culturing. Cultures having no noticeable growth of bacteria after 15 days were considered negative. Contamination was very common, see Table II. These tests were carried out at least three separate times with essentially similar results. From several lots, samples were taken from many different serum bottles (maximum 12 bottles from a single lot). The results were again unanimous, although small variation of the degree of contamination was noticeable between bottles.

TABLE I

MEDIUM RPMI 1640 FORMULA

| Composition: | mg/l |
|---|---|
| Amino acids[1] | |
| L-Arginine | 200.0 |
| L-Asparagine.$H_2O$ | 56.82 |
| L-Aspartic acid | 20.0 |
| L-Cystine.2HCl | 66.17 |
| L-Glutamine | 300.0 |
| L-Glutamine acid | 20.0 |
| Glycine | 10.0 |
| L-Histidine | 15.0 |
| L-Hydorxyproline | 20.0 |
| L-Isoleucine | 50.0 |
| L-Leucine | 50.0 |
| L-Lysine.HCl | 40.0 |
| L-Methonine | 15.0 |
| L-Phenylalanine | 15.0 |
| L-Proline | 20.0 |
| L-Serine | 30.0 |
| L-Threonine | 20.0 |
| L-Tryptophan | 5.0 |
| L-Tyrosine | 20.0 |
| L-Valine | 20.0 |
| Vitamins | |
| D-Biotin | 20.0 |
| Ca-D(+)-pantothenate | 0.25 |
| Choline chloride | 3.0 |
| Folic acid | 1.0 |
| myo-Inositol | 35.0 |
| Nicotinamide | 1.0 |
| p-Aminobenzoic acid | 1.0 |
| Pyridoxine.HCl | 1.0 |
| Riboflavin | 0.20 |
| Thiamine.HCl | 1.0 |
| Vitamin B12 | 0.005 |
| Other components[2] | |
| D(+)-Glucose | 2000.0 |
| Glutathione | 1.0 |
| Phenol red, Ha | 5.0 |
| Inorganic Salts[3] | |
| $CA(NO_3)_2.4H_2O$ | 100.0 |
| KCl | 400.0 |
| $MgSO_4.7H_2O$ | 100.0 |
| NaCl | 6000.0 |

TABLE I-continued

MEDIUM RPMI 1640 FORMULA

| Composition: | mg/l |
| --- | --- |
| Na$_2$HPO$_4$.2H$_2$O | 1003.6 |
| NaHCO$_3$ | 2000.0 |

TABLE II

List of sera tested for contamination

| serum | manufacturer | lot no. | culture result |
| --- | --- | --- | --- |
| FBS | Imperial | 861163 | +++ |
| FBS | Imperial | 460865 | +++ |
| HS | Imperial | 260652 | +++ |
| NBS | Imperial | 360373 | +++ |
| FBS | Gibco | 20Q4380X | ++ |
| FBS | Gibco | 40F0982F | +++ |
| FBS | Gibco | 30F0484F | + |
| FBS | Gibco | 10G8289Y | +++ |
| FBS | Gibco | 10G7572F | — |
| FBS | Gibco | 10G3673Y | — |
| FBS | Gibco | 10F7380F | — |
| FBS | Gibco | 50Q1676X | + |
| FBS | Gibco | 10FO484Y | +++ |
| NBS | Gibco | 10Q3380 | + |
| NBS | Gibco | 30A1078 | + |
| FBS | BM | 613594 | + |
| FBS | BM | 210463 | + |
| FBS | BM | 870910 | + |
| FBS | Nord Vacc | Moo 196-7 | + |
| FBS | Sera-Lab | 701112 | + |
| FBS | Sera-Lab | 701113 | + |
| FBS | Sera-Lab | 601129A | +++ |
| FBS | Sera-Lab | 801114 | +++ |
| HumS | FRC | 2059-7001 | ++ |
| HS | FlowLab | 026017 | ++ |
| FBS | FlowLab | 028011 | + |

+++: coccoid particles after cultivation of one day, ++: coccoid particles after cultivation of five days, +: coccoid particles after cultivation of ten days.
Imperaial = Imperial Laboratories, U.K.
Gibco = Gibco Limited, Paisley, Scotland
BM = Boehringer Mannheim, F.R.G.
Nord Vacc = Nord Vacc, Skärholmen, Sweden
Sera-Lab = Sera-Lab LTD, Crawley Down, Sussex, England
FRC = Finnish Red Cross, Helsinki, Finland
Flow Lab = Flow Laboratories LTD, Ayshire, Scotland
NBS = newborn bovine serum
FBS = fetal bovine serum
HS = horse serum
HumS = human serum (sterile filtered pooled serum available from Finnish Red Cross)

EXAMPLE II

Possible presence of cell culture contaminants belonging to genus Nanobacterium or Mycoplasma in cultured cells was tested by the 3T6 indicator cell culture method. Samples of cell cultures to be tested (medium together with some cells) were taken using standard sterile techniques and stored at +4° C. up to one week until tested. 3T6 cultures were prepared as follows: 3T6 cells (obtained from ATCC [code No. CCL 96] and tested to be free of contaminants) were cultured under sterile conditions in DMEM with 2mM L-glutamine and supplemented with 10% gamma-irradiated fetal bovine serum (tested to be free of Nanobacteria). Antibiotics were not used. Cultures were incubated at 37° C. with an atmosphere of 10% CO$_2$-90% air at 90% humidity. Cells near confluency were washed, trypsinized, collected and washed, and then counted. All of this was carried out using standard cell culture procedures. Approximately 3,000 cells were suspended in 0.5 ml of the culture medium (described above) and transferred to a special track bottle (Sterilin, Feltham, England, order No. 129AX/1). After incubation for 16 hours under cell culture conditions, 3T6 cells were attached to the cover glass on the bottom of the vessel. Then a sample of 100 µl to 500 µl of the material to be tested was added to the culture. Control cultures of 3T6 (sterile) were prepared by adding only culture medium, and contaminated control cultures were prepared by adding either Nanobacteria or Mycoplasma to cultures. All controls were incubated, treated and stained exactly as the test sample.

After culture, all steps were carried out at room temperature. Culture medium was removed and cover slips were washed gently twice with 1 ml of phosphate buffered saline for 1 minute (for each washing). Saline was removed and 0.5 ml of 3% formaldehyde solution (in phosphate buffered saline) was added for 30 minutes. Fixative was then removed and the cover slip was washed with phosphate buffered saline. The cover slip was then incubated with 0.5 ml of 0.5% Triton X-100 in phosphate buffered saline for 10 minutes. After removal of this solution, Hoechst 33258 stain together with FIT coupled anti-Nanobacteria antibody was added in 0.5 ml of phosphate buffered saline. Final concentration of Hoechst 33258 was 0.5 mg/l. Anti-Nanobacteria serum was obtained by immunizing rabbits with purified Nanobacteria. IgG-fraction of their serum was obtained using Protein A affinity chromatography (Pharmacia, Uppsala, Sweden). IgG was then labelled with fluorescein isothiocyanate (FITC) using the published standard coupling techniques. A preliminary test was constructed to determine the best dilution of FITC coupled anti-Nanobactria antibody in the staining procedure. That depended on the particular antibody lot, of course, but was in this case 30 µg IgG protein/ml. So this amount of antibody was added to the staining solution. FITC coupled antibody solutions and stained preparations were kept protected from light until microscopy.

After incubation for 30 minutes (in a dark room), the cover slips were removed from the track bottle, washed thoroughly with phosphate buffered saline in a dish with 5 buffer exchanges (for 10 minutes) again protected from strong light. A cover slip was then mounted on an objective glass cell side facing the mounting medium. As mounting medium, 50% glycerol in phosphate buffered saline, preferably containing 0.5% n-propyl gallate can be used. Alternatively, suitable commercial mounting media can be used (e.g., Mount Quick "Aquous" Daido Sangyo Co, Tokyo, Japan). The preparations were then viewed by standard fluorescence microscopy using commonly available filter sets intended for use with the Hoechst 33258 stain and for the FITC label (different filters are used).

The result of the test was as follows:

Control 3T6 indicator cells—No cytoplasmic or extracellular staining by Hoechst or by FITC.

Mycoplasma added controls—Strongly blue cytoplasmic and extracellular fluorescent dots visualized by Hoechst filter set. No FITC fluorescence.

Nanobacteria added controls—Cytoplasmic and extracellular fluorescent dots revealed by Hoechst filter set. Typically, cytoplasmic dots outnumber extracellular dots. The fluorescence intensity of Nanobacteria was slightly lower than that of mycoplasma. FITC filter set revealed strong yellow-greenish fluorescence. FITC positive dots were also Hoechst positive.

3T6 with the cell culture test samples—Some of the samples were identical to negative controls. These samples were also negative in Mycoplasmas and Nanobacteria testing by specific culture methods. Mycoplasmas were cultured on mycoplasma agar as described by Barile et al. (The identification and sources of mycoplasmas isolated from contaminated cell cultures, *Annals of the New York Academy of Sciences,* Vol. 225, 251-264 (1973)) and Nanobacteria with the method in Example I.

Some samples showed either positive Hoechst or FITC labelling. Interestingly, both Mycoplasma and Nanobacteria labels were positive on some. Nanobacteria can be identified specifically with the specific FITC coupled antibody to Nanobacteria. Only Nanobacteria fluoresced. Both Mycoplasmas and Nanobacteria fluoresced in Hoechst staining. Thus, the present method could indicate rapidly and specifically whether Mycoplasmas or Nanobacteria were present.

While the invention has now been described with reference to several preferred embodiments, those skilled in the art will appreciate that various substitutions, omissions, modifications and changes may be made without departing from the scope or spirit thereof. Accordingly, it is intended that the foregoing description be considered merely exemplary of the invention and not a limitation thereof.

What is claimed is:

1. A biologically pure culture of Nanobacterium.

2. A biologically pure culture of Nanobacterium as deposited with DMS as deposit numbers 5819, 5820 or 5821.

3. A process for the cultivation and replication of Nanobacterium, said process comprising inoculating a tissue culture medium with a biological sample, said biological sample being derived from animal or human blood, serum, tissue or tissue fluids, under conditions sufficient to promote the growth of Nanobacterium and culturing said inoculated medium for a time sufficient to allow replication.

4. The process as claimed in claim 3, wherein the tissue culture medium is RPMI 1640.

5. The process as claimed in claim 3, wherein the tissue culture medium further comprises D,L-selenomethionine and nucleotide precursors.

6. A method for detecting the presence of Nanobacterium in a biological sample, said method comprising:
   a) inoculating a tissue culture with a biological sample, said biological sample being derived from animal or human blood, serum, tissue or tissue fluids;
   b) culturing Nanobacterium which may be present in the biological sample under conditions sufficient to promote the growth of said bacteria and for a time sufficient to allow replication of said bacteria;
   c) staining said culture with a nucleic acid stain with pretreatment of the culture using a fixative;
   d) providing a gamma-irradiated Nanobacterium as a control; and
   e) comparing the stained culture of step c) with the control of step d) to detect the presence of Nanobacterium in the biological sample.

7. The process as claimed in claim 6, wherein the tissue culture medium is RPMI 1640.

8. The process as claimed in claim 6, wherein the tissue culture medium further comprises D,L-selenomethionine and nucleotide precursors.

9. The process as claimed in claim 6, wherein the tissue culture medium contains fetal bovine serum.

10. The process as claimed in claim 6, where detection is verified with the use of antibodies specific to Nanobacteria.

11. A test kit comprising indiscreet containers:
   a) a tissue culture medium sufficient for allowing the culture of Nanobacterium;
   b) gamma-irradiated bacteria of Nanobacterium as a control wherein the dose of irradiation was in the range of about 2.5 to 4.0 megarads; and
   c) a nucleic acid stain suitable for staining Nanobacterium.

12. The test kit as claimed in claim 11, further comprising a supplement.

13. The test kit as claimed in claim 12, wherein the supplement is D,L-selenomethionine and nucleotide precursors.

14. The test kit as claimed in claim 11, further comprising gamma-irradiated fetal bovine serum.

15. The test kit as claimed in claim 11, wherein the tissue culture medium is RPMI 1640.

16. The test kit as claimed in claim 11, where detection is verified with specific antibodies recognizing Nanobacteria, made visible with a fluorescent or enzymatic label or a fluorescent detection system.

17. The test kit as claimed in claim 16, wherein a 3T6 indicator cell culture is used.

18. A method for detecting the presence of Nanobacterium in a biological sample derived from animal or human blood, serum, tissue or tissue fluids, said method comprising:
   a) filtering said biological sample through a 0.22 μm filter,
   b) recovering Nanobacterium from the filter and
   c) determining the presence of Nanobacterium by immunological methods or by DNA staining.

19. A process for the purification of Nanobacteria, said process comprising immobilizing antibodies recognizing Nanobacterial antigens on a surface, exposing a biological sample comprising animal or human blood, serum, tissue or tissue fluids to said immobilized antibodies and recovering Nanobacteria from the immobilized antibodies.

20. A process for the preparation of Nanobacterium specific antiserum, said process comprising:
   a) culturing Nanobacteria according to the process of claim 3;
   b) harvesting Nanobacteria;
   c) incubating the Nanobacteria with proteinase K;
   d) recovering Nanobacteria;
   e) solubilizing the Nanobacteria by incubation with a strong acid to obtain a solubilized antigenic preparation;
   f) injecting said solubilized antigenic preparation into an animal; and
   g) harvesting the antiserum.

21. A process for the in vitro removal of Nanobacteria from a biological sample comprising animal or human blood, serum, tissue or tissue fluids, said process comprising exposing Nanobacteria to a Nanobacteria-specific antibody and recovering Nanobacteria from said biological sample.

22. A process for the in vitro removal of Nanobacteria from a biological sample, said process comprising exposing a biological sample comprising animal or human blood, serum, tissue or tissue fluids to a Nanobacteria-specific antibody in an immunofluorescent assay or treatment.

23. The method of claim 6 wherein said fixative of step c) is glutaraldehyde.

24. The method of claim 6 wherein said fixative of step c) is formaldehyde.

* * * * *